United States Patent
Dose

(10) Patent No.: US 9,670,318 B2
(45) Date of Patent: Jun. 6, 2017

(54) BRIGHT FLUOROCHROMES BASED ON MULTIMERIZATION OF FLUORESCENT DYES

(71) Applicant: Miltenyi Biotec GmbH, Bergisch Gladbach (DE)

(72) Inventor: Christian Dose, Kurten (DE)

(73) Assignee: Miltenyi Biotec GmbH, Bergisch Gladbach (DE)

( * ) Notice: Subject to any disclaimer, the term of this patent is extended or adjusted under 35 U.S.C. 154(b) by 85 days.

(21) Appl. No.: 14/723,505

(22) Filed: May 28, 2015

(65) Prior Publication Data

US 2016/0347907 A1    Dec. 1, 2016

(51) Int. Cl.
C08G 65/48 (2006.01)

(52) U.S. Cl.
CPC ..................... *C08G 65/48* (2013.01)

(58) Field of Classification Search
CPC .................. C08L 1/02; C09B 19/005
See application file for complete search history.

(56) References Cited

U.S. PATENT DOCUMENTS

| | | | |
|---|---|---|---|
| 5,268,486 A | 12/1993 | Waggoner et al. | |
| 6,130,101 A | 10/2000 | Mao et al. | |
| 6,913,743 B2 | 7/2005 | Licha et al. | |
| 6,977,305 B2 | 12/2005 | Leung et al. | |
| 7,655,217 B2 | 2/2010 | Licha et al. | |
| 2012/0052506 A1 | 3/2012 | Yue et al. | |
| 2015/0119553 A1 | 4/2015 | Xu et al. | |

FOREIGN PATENT DOCUMENTS

| | | |
|---|---|---|
| WO | WO 2006/031851 | 3/2006 |
| WO | WO 2006/125736 | 11/2006 |
| WO | WO 2008/009579 | 1/2008 |
| WO | WO2009078970 | 6/2009 |
| WO | WO 2011/075729 | 6/2011 |
| WO | WO 2012/119859 | 9/2012 |
| WO | WO2013056720 | 4/2013 |
| WO | WO 2013/092774 | 6/2013 |

OTHER PUBLICATIONS

Reichert, Dissertation, Freie Universitat Berlin, Synthesis of Hyperbranched Polyglycerol Dye Conjugates for in vitro and in vivo Targeting Studies, 2011, pp. I-127.*

Zaragoza Dorwald, Side Reactions in Organic Synthesis, 2005, Wiley-VCH Verlag GmbH & Co. KGaA, Weinheim, Preface. p. IX.*

* cited by examiner

*Primary Examiner* — Paul A Zucker
(74) *Attorney, Agent, or Firm* — Jaquelin K. Spong

(57) ABSTRACT

The invention is directed to a fluorescent dye according to the general formula I:

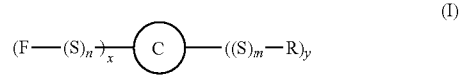

with
 C is a core moiety comprising 20 to 200 atoms;
 S same or different ether residues comprising 1 to 10 carbon atoms;
 n is an integer ranging from 2 to 500;
 m is an integer ranging from 0 to 500;
 x is an integer ranging from 2 to 50;
 y is an integer ranging from 1 to 50;
 R same or different residue comprising a reactive group capable of forming a covalent bond with a biomolecule;
 F same or different fluorophores covalently bound to $(S)_n$.

The fluorescent dyes can be conjugated to a biomolecule and used for flow cytometry and/or by fluorescence microscopy.

7 Claims, 9 Drawing Sheets

BRIGHT FLUOROCHROMES BASED ON MULTIMERIZATION OF FLUORESCENT DYES

CROSS REFERENCE TO RELATED APPLICATIONS

Not applicable.

STATEMENT REGARDING FEDERALLY SPONSORED RESEARCH

Not applicable.

STATEMENT REGARDING MICROFICHE APPENDIX

Not applicable.

BACKGROUND

The present invention is directed to fluorescent dyes with increased brightness and methods of use thereof.

Fluorescent dyes conjugated to antibodies are commonly used for immunofluorescence analysis. A vast number of variants in antibodies, fluorescent dyes, flow cytometers, flow sorters and fluorescence microscopes has been developed in the last two decades to enable specific detection and isolation of target cells. One issue in immunofluorescence technology is the detection threshold of the fluorescence emission, which can be enhanced, for example, by better detectors, filter systems or modified fluorescent dyes.

A limitation of conventional small molecule fluorescent dye molecules is their limited brightness. Therefore biomolecules are typically labeled with multiple dye molecules to increase the brightness of the fluorochrome conjugate. Most of the aforementioned fluorescent dye molecules, such as rhodamines or cyanines, contain planar aromatic chromophores, which are prone to hydrophobic interactions leading to dye-dye dimers with low or no fluorescence. Consequently, fluorescence intensity of labeled biomolecules is not proportional to the degree of fluorescent dye labeling of said biomolecules. At higher degrees of labeling (DOLs) the fluorescence intensity of the single dye might even decrease due to self-quenching mechanism caused by dimer, trimer or multimer formation.

These undesired formations have been reduced to some extent by adding substituents to the flat aromatic dye molecules, which increase water solubility. Suitable substituents described in the literature might impart charges to the dye molecule, such as sulfonate groups described, e.g., in U.S. Pat. Nos. 5,268,486 and 6,977,305, 6,130,101 and Panchuk-Voloshina, et al., J. Histochem. Cytochem. 47(9), 1179 (1999), or phosphate groups described, e.g., in WO2013056720. Other suitable dimerization reducing substituents are bulky water-soluble polymers, such as polyethylene glycol described, e.g., in patent application WO2009078970, or charged dendrimers described, e.g., in U.S. Pat. Nos. 6,913,743, and 7,655,217. Although biomolecule conjugates of these substituted dyes achieve higher brightness at higher degrees of labeling (DOLs) than conjugates of the unsubstituted parent dyes, there is still a deviation from a linear proportionality between fluorescence intensity and degree of labeling of the labeled biomolecule albeit at a higher DOL as for the unsubstituted parent dye.

Conjugate brightness is also limited by the number of functionalization sites available on the biomolecule, which can be functionalized without loss of biomolecule activity. As a result DOLs of biomolecule conjugates are still limited, e.g., for antibodies (IgG) they are typically in the range of 4 to 8 in the case of hydrophilic labels (R. P. Haugland, Current Protocols in Cell Biology (2000) 16.5.1-16.5.22). Consequently the brightness of these conjugates is still inferior to, e.g., conjugates of phycobiliproteins, such as phycoerythrin (PE) or allophycocyanine (APC).

The high fluorescence intensity of phycobiliproteins and their biomolecule conjugates is due to the presence of multiple fluorophore subunits within a phycobiliprotein. R-phycoerythrin, e.g., contains 34 phycobilin fluorophore subunits (A. N. Glazer, J. Appl. Phycol. 6, 105 (1994)). Therefore biomolecule conjugates of phycobiliproteins, such as PE or APC are popular, e.g., in flow cytometry, despite their drawbacks stemming from their protein nature such as limited stability against non-physiological solvents, temperature, and pH values as well as their limited photostability and their generally limited shelf life. Another drawback is the limited availability of different colors, which limit multiplexing capabilities within a single fluorescence assay.

There have been efforts to construct multichromophore constructs with phycobiliprotein-like fluorescence properties by arranging fluorophores into precise supramolecular structures preventing self-quenching of excited fluorophores. Benvin et al., J. Am. Chem. Soc. 129(7), 2025 (2007) describe fluorescent dyes intercalated into supramolecular DNA templates. However, a drawback of this method is the non-covalent binding of the fluorophores within the DNA scaffold. Migration of dye molecules out of the DNA scaffold can lead to loss of fluorescence signal. In case of a multicolor experiment dye exchange between differently labeled DNA scaffolds might lead to false positive fluorescent signals. In case of a multiparameter experiment employing multiple colors it is advisable to use covalently bound fluorophores.

Another class of brightly fluorescent dyes for biomolecule labeling are fluorescent polymers based on semiconducting polymers, such as polyfluorenes described e.g. in U.S. Pat. Nos. 8,158,444, 8,354,239, and 8,802,450 and 8,362,193, 8,455,613, and 8,575,303. These polymers also contain multiple fluorophore subunits, as the effective conjugation length within the polymer is limited to 9-10 monomer subunits.

Preparing brighter fluorescent dyes by multimerizing conventional fluorescent dye molecules on a water-soluble scaffold has so far not resulted in compounds useful for the labeling of biomolecules. Recommendations for fluorescent labeling of, e.g., dextrans are 0.3-0.7 dye molecules per dextran in the 3000 MW range, 0.5-2 dye molecules in the 10,000 MW range, 2-4 dye molecules in the 40,000 MW range and 3-6 dye molecules in the 70,000 MW range. Due to their large size and bulkiness these dye multimers offer no benefit in biomolecule labeling and are unsuitable for preparing biomolecule conjugates with phycobiliprotein-like fluorescence intensities. Fluorescently labeled dextrans with higher degree of labeling show quenching due to dye-dye interaction. This has found use in U.S. Pat. No. 5,719,031, wherein the degree of labeling of dextran-fluorochrome-conjugates is high enough to furnish fluorescent quenching. Enzymatic degradation of the dextran-fluorochrome-conjugate is accompanied by an enhancement of the fluorescence emission signal, which is used for quantification of the enzymatic digestion process.

There remains still a considerable need for improved fluorescent dyes for labeling of biomolecules, which provide phycobiliprotein-like fluorescence intensity without the limitations of phycobiliproteins and fluorescent polymers.

SUMMARY

It was therefore an object of the invention to provide a fluorescent dye label with high fluorescence intensity, low unspecific background staining and stability against fixation.

Surprisingly, it was found that fluorescent dyes multimerized on branched polyether scaffolds, such as multi-arm polyethylene glycols, are highly fluorescent without noticeable quenching. In addition, the polyether scaffold seems to reduce the tendency of fluorescent dyes to bind unspecifically.

One aspect the invention allows for tailoring the properties of the fluorescent dye label regarding photostability and stability against different environmental conditions such as temperature, pH and solvent. In another aspect of the invention a broad range of different excitation and emission wavelengths are provided. In another aspect of the invention retention of biomolecule activity is provided despite a high number of fluorophore subunits present in the biomolecule-fluorescent dye conjugate.

With the present invention, it is possible to introduce a high degree of fluorophore labeling to a biomolecule without loss of activity or increased unspecific binding, e.g., in case of antibodies a fluorophore DOL of greater than 10, preferably equal or greater than 15 is achieved, resulting in an antibody fluorochrome conjugate with phycobiliprotein-conjugate-like fluorescence intensity and low unspecific background staining.

Accordingly, an object of the invention are fluorescent dyes according to the general formula I:

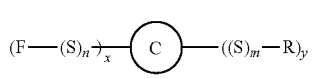

(I)

with

C is a core moiety comprising 20 to 200 atoms;

S same or different ether residues comprising 1 to 10 carbon atoms;

n is an integer ranging from 2 to 500;

m is an integer ranging from 0 to 500;

x is an integer ranging from 2 to 50;

y is an integer ranging from 1 to 50;

R same or different residue comprising a reactive group capable of forming a covalent bond with a biomolecule;

F same or different fluorophores covalently bound to $(S)_n$.

The core moiety C provides multiple (x+y) attachment points for the polyether residues $(S)_n$ and $(S)_m$. R comprises a reactive group capable of forming a covalent bond with a biomolecule which recognizes cellular structures like antigens.

BRIEF DESCRIPTION OF THE DRAWINGS

Various exemplary details are described with reference to the following figures, wherein:

FIGS. 1a-1e show a comparison of dot plots of peripheral blood mononuclear cells (PBMC) stained with CD4 antibody (clone Vit4) conjugated with: FIG. 1a fluorescein isothiocyanate (FITC); FIG. 1b fluorescein multimerized with a branched PEG (PEG-FAM); FIG. 1c Alexa Fluor 488 (AF488); FIG. 1d Alexa Fluor 488 multimerized with a branched PEG (PEG-AF488), and FIG. 1e R-phycoerythrin (PE) measured by flow cytometry.

In all figures, fluorescent dyes with PEG subunits are according to the invention.

DETAILED DESCRIPTION

The fluorescent dyes according to the invention can be prepared by standard chemistry known to the person skilled in the art and as further disclosed in the examples of the present patent application.

By way of example, preferred fluorescent dyes according to the invention are shown in the following general formula II and III:

(II)

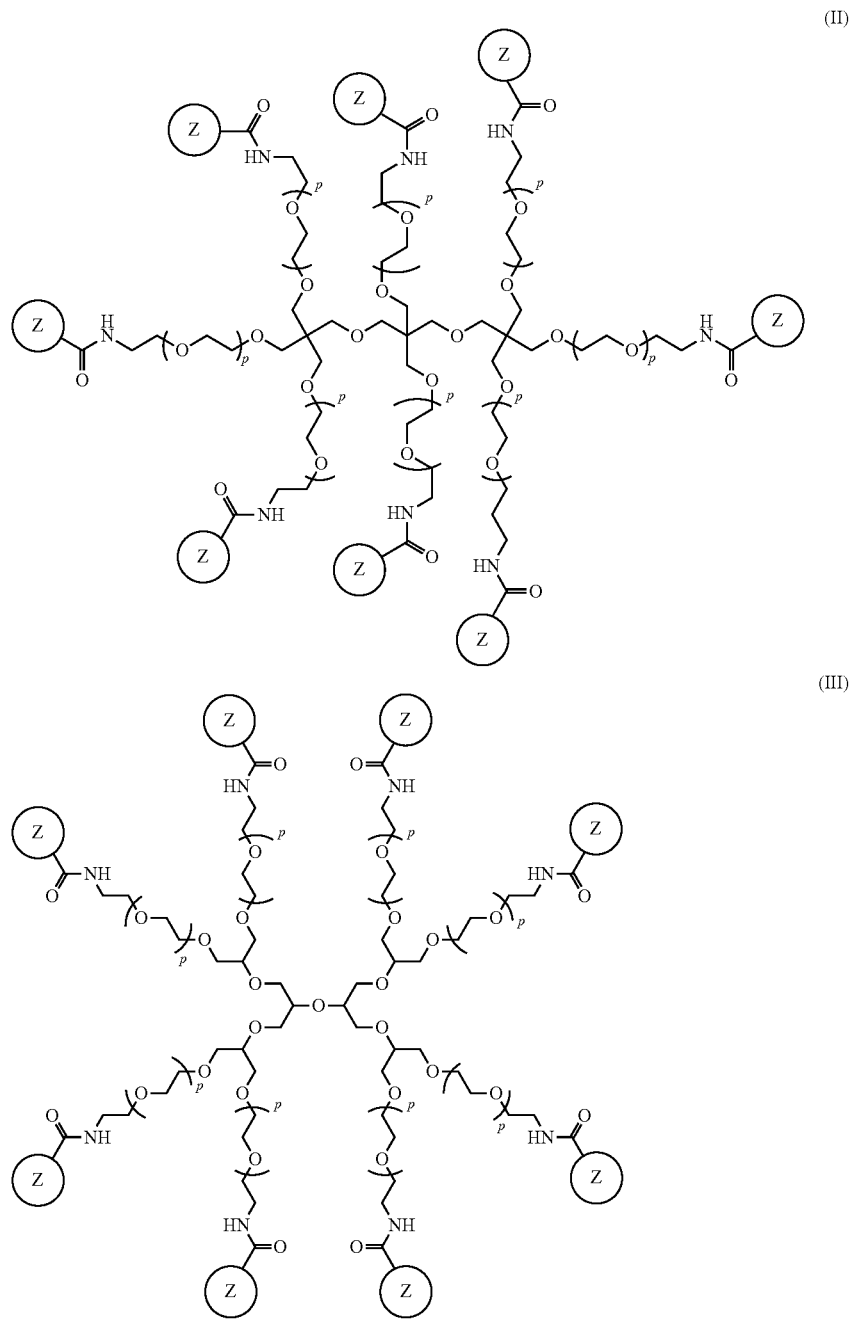

(III)

In formula (II) and (III), Z is at least one of F and R and p is at least one of n and m (depending on whether the respective polyether branch binds to F or R, with the provision that at least two F and at least one group R are comprised. F, R, n and m have the meaning as already disclosed.

Fluorophore F

The fluorophore F used in the present invention is coupled to the core moiety C via the polyether scaffold and may be any organic fluorescent dye molecule. Typically, such fluorophores have found use as laser dyes in organic dye lasers. Substituted versions, which can be conjugated to biomolecules, have found use as labels in flow cytometry and fluorescence microscopy.

Preferably, the fluorophore F is selected from the group consisting of xanthene dyes, rhodamine dyes, coumarine dyes, cyanine dyes, pyrene dyes, oxazine dyes, pyridyl oxazole dyes and pyrromethene dyes.

Figure 2:
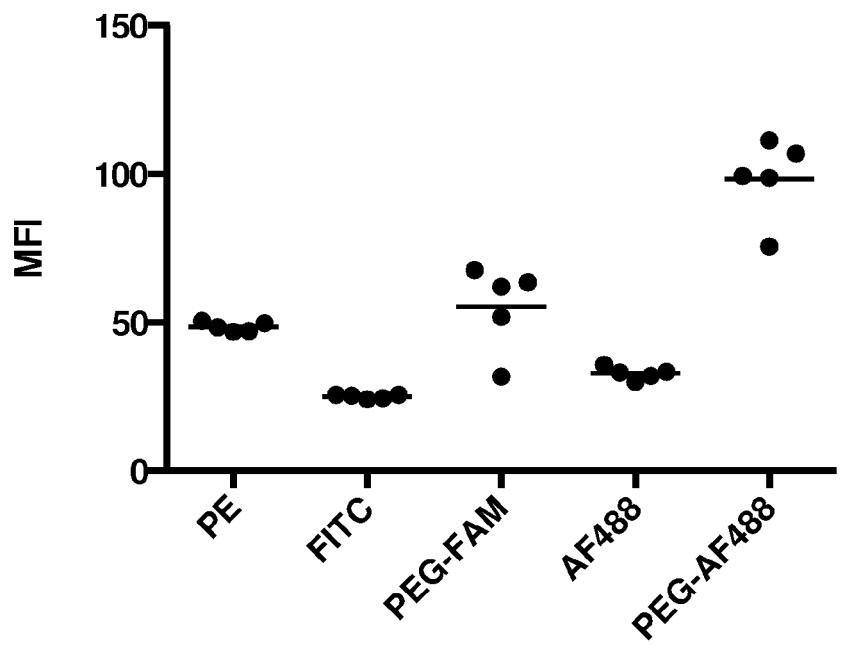
FIG. 2 shows the median fluorescence intensities (MFI) and stain indices (SI) of T helper cells (CD4 bright positive) of five different donors stained with CD4 antibody (clone Vit4) conjugated with FITC, fluorescein multimerized on a branched PEG (PEG-FAM), Alexa Fluor 488 (AF488), Alexa Fluor 488 multimerized on a branched PEG (PEG-AF488) or PE measured by flow cytometry.
Figure 2:
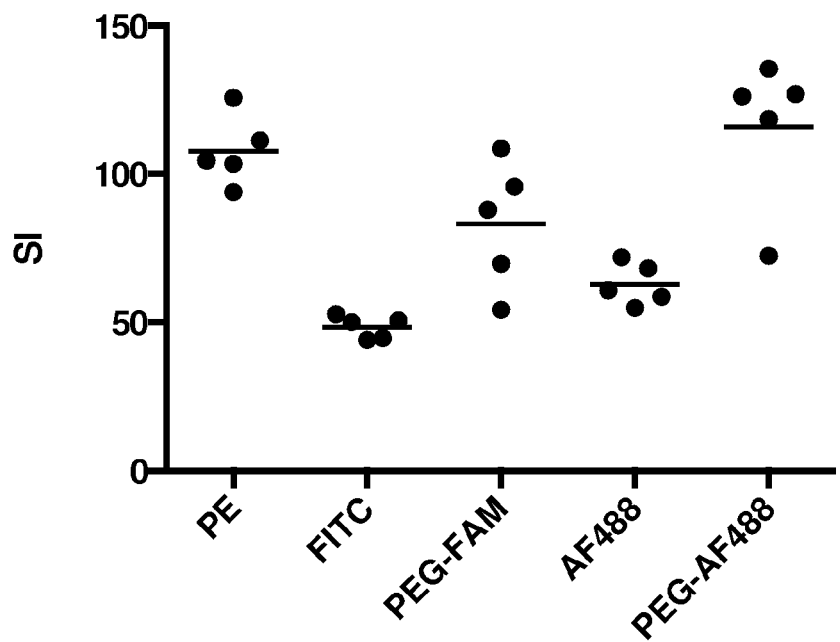

In a variant of the invention, the fluorophore F is substituted with one more water solubility imparting substituents selected from the group consisting of sulfonates, phosphonates, phosphates, polyethers, sulfonamides and carbonates. It is particularly advantageous to use fluorescent dyes with sulfonate substituents, such as dyes of the Alexa Fluor family provided by Thermo Fisher Scientific Inc. The degree of sulfonate substitution per fluorophore may be 2 or more, i.e., for rhodamine dyes or cyanine dyes. The use of sulfonated dyes compared to unsulfonated dyes leads to even brighter conjugates of fluorophores multimerized on a polyether scaffold as can be seen in FIG. 2: T helper cells stained with a CD4 conjugate of Alexa Fluor 488 multimerized on a branched PEG (PEG-AF488) are almost twice as bright (mean MFI 98) as T helper cells stained with a CD4 conjugate of fluorescein multimerized on a branched PEG (PEG-FAM) (mean MFI 55).

The fluorophores F can be attached to the polyether scaffolds by methods known in the art, i.e., by reacting a fluorescent dye with a group reactive towards amino or thiol groups with a branched polyether scaffold with amino end groups.

Core Moiety C

The core moiety C may be any structure comprising 1 to 100 carbon atoms, which allows attachment of x+y polyether residues $(S)_n$ and $(S)_m$.

Useful core moieties for the invention are polyhydroxy compounds, polyamino compounds and polythio compounds. Preferred are polyhydroxy compounds, such as pentaerythritol with four hydroxyl group as attachment points for 3 to 4 polyether residues via ether bonds, dipentaerythritol with six hydroxyl groups as attachment points for 3 to 6 polyether branches via ether bonds, tripentaerythritol or hexaglycerol with eight hydroxyl groups as attachment points for 3 to 8 polyether branches via ether bonds.

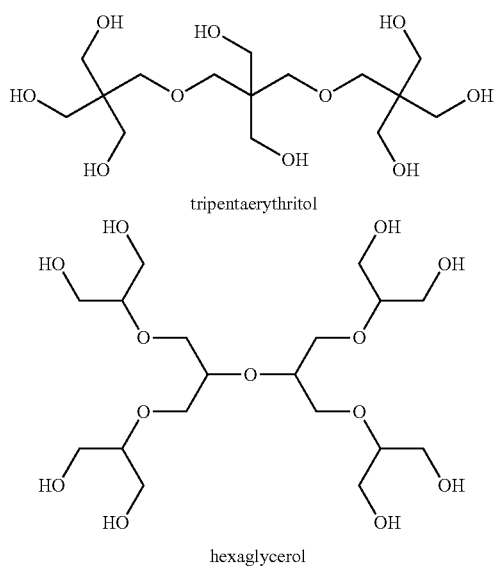

tripentaerythritol hexaglycerol

Polyether Residues S

The polyether residues $(S)_n$ and $(S)_m$ consist of ether monomer units S which may each containing 1 to 10, and preferably 1 to 4 oxygen atoms per monomer subunit S. These polyether branches might be homopolymeric or copolymeric, i.e., alternating or block copolymers. Polyether residues $(S)_n$ and $(S)_m$ can be linear or branched, especially in the case when monomer units S with 2 or more oxygen atoms are used. In a preferred embodiment of the invention, the polyether residues comprise polyethylene glycol chains, i.e., S stands for the residue $CH_2CH_2O$— and n, m are independently integers ranging from 10 to 200.

In a particular useful embodiment of the invention commercially available multi-arm polyethylene glycols (branched PEGs) serve as scaffolds including core moiety and polyether branches. Multi-arm polyethylen glycols are commercialized by, for example, Nanocs Inc. or NOF Corporation.

Reactive Groups R

The fluorescent dyes according to the invention are attached to biomolecules via groups R, comprising a reactive group. Groups R shall be capable of forming covalent bonds via the reactive group of the biomolecule, with functional groups, like amino and thiol groups. Either R or $(S)_m/(S)_n$ comprise a subunit capable of forming a covalent bond with the respective other group. For example, polyether groups $(S)_m/(S)_n$ are commercially available with amino end groups, which can react, for example, with an R group comprising a carboxy function. A person skilled in the art will have no difficulty in selecting the appropriate chemistry. Examples for R comprising such reactive groups are, e.g., active esters, such as N-hydroxysuccinimid ester, tetrafluorophenyl ester, pentafluorophenyl ester, sulfodichlorophenyl ester, imido ester, isothiocyanate, isocyanate, sulfonyl halides, acyl halides, acyl azide, monochlorotriazine, dichlorotriazine, aldehyde, glyoxal, maleimide, iodoacetamide, hydrazine, azidonitrophenyl, phosphoramidite, alkyne, alkyl azide, diene or allyl groups.

Covalent bond formation is also possible via reactive groups R, which are functional groups capable of reacting with a reaction substrate carrying a suitable reactive group. Functional groups suitable for coupling reactions may be comprised, e.g., of an amino group, a thiol group, a hydroxyl group, or a carboxyl group.

It is also conceivable to use additional reactive groups R' on polyether branches with low reactivity, with the purpose of keeping apart fluorophores to prevent dye-dye interactions. These low-reactive groups R' may be hydrogen atom, an alkyl group, a trifluoroalkyl group, an aryl group, a halogen group, a sulfonyl group, a sulfonate group, a phosphonate group, a sulfonamide group, or combinations thereof. At least one of the above mentioned reactive groups R is necessary for the performance of the fluorescent dyes according to the invention.

Fluorescent Biomolecule Conjugates

Another object of the invention are fluorescent biomolecule conjugates comprising one or more fluorescent dyes as already disclosed conjugated via group R to at least one biomolecule selected from group consisting of immunoglobulin, antibody, fragmented antibody, Fab, Fab', F(ab')2, sdAb, scFv, di-scFv, each naturally or recombinant.

The biomolecule conjugates of the invention are either prepared by reacting a biomolecule with a reactive group R of the fluorescent dye or by reacting an activated biomolecule with a suitable functional group R of the fluorescent dyes.

Biomolecules suitable for conjugation with the fluorescent dye of the invention may be proteins, peptides, carbohydrates, nucleic acids, lipids and combinations thereof. These biomolecule are capable of binding to binding partners, such as analytes, cell surface markers, antigens etc., in order to label, detect and quantify said analytes, cell surface markers, antigens etc.

Fragmented antibodies may be synthesized by recombinant procedures including covalent and non-covalent conjugates containing these kinds of molecules.

In one embodiment of the invention, the biomolecule is selected from a group consisting of peptide/MHC-complexes, receptors for cell adhesion or costimulatory molecules, receptor ligands, antigens, hapten binders, avidin, streptavidin, neutravidin, aptamers, primers and ligase substrates. Preferably, receptors are moieties e.g., for cell adhesion or costimulatory molecules and hapten binders are avidin, streptavidin or neutravidin. Nucleic acids may be, e.g., aptamers, primers, or substrates for ligases.

Biotin binders, such as avidin, streptavidin or neutravidin labeled with fluorophore labeled branched polyether scaffold allow for a sensitive detection via biotinylated primary detection molecules due to an additional multiplying effect of the multiple biotinylation of said primary detection molecule.

In one embodiment of the invention the biomolecule is an IgG antibody with 2 to 7 fluorescent polyether labels carrying each 4 to 6 fluorophore groups, resulting in fluorophore DOLs of 8 to 40 dye molecules per antibody molecule, preferably a fluorophore DOL of more than 10, most preferably a DOL of 15 or more fluorophore units.

In yet another embodiment of the invention, the biomolecule conjugates comprise one or more fluorescent dyes wherein at least one biomolecule is conjugated with 2 to 20 fluorescent dyes comprising each 1 to 10 fluorophores F, inclusive. It is preferred that more than one fluorescent dye is present in the biomolecule conjugates.

INDUSTRIAL APPLICABILITY

The biomolecule conjugates and/or the fluorescent dyes of the invention are especially useful for detection, counting or separation of cells utilizing a certain set of antigens recognized by the biomolecule conjugate.

Another object of the invention is therefore a method of analyzing cells or tissue labeled by the fluorescent biomolecule conjugates according to the invention by flow cytometry and/or by fluorescence microscopy. Accordingly, the method may include labeling with the fluorescent biomolecule conjugates as described, and performing at least one of flow cytometry and fluorescence microscopy.

In another embodiment of the invention one or more populations of labeled cells are detected from the sample and separated as target cells. Preferably the cells detected by the conjugate are separated from the sample by electrostatic forces, piezoelectric forces, mechanical separation or optoacoustic means. Suitable for such separations are especially flow sorters, e.g., FACS or MEMS-based cell sorter systems, for example, as disclosed in EP14187215.0 or EP14187214.3.

In another embodiment of the invention the location of the binding target of biomolecule conjugates on cell or tissue samples is determined by fluorescence microscopy. Suitable methods of fluorescence microscopy include epifluorescence microscopy, confocal laser scanning microscopy, multi photon microscopy, total internal reflection fluorescence (TIRF) microscopy, single plane illumination microscopy (SPIM) and super resolution microscopy methods such as, e.g., stimulated emission depletion (STED) microscopy, stochastic optical reconstruction microscopy (STORM), photo activated localization microscopy (PALM), or spatially modulated illumination (SMI) microscopy.

EXAMPLES

Example 1

Step A: Preparation of AF488 Multimerized on an 8-Arm PEG (PEG-AF488)

Amino-PEG (8-arm) was dissolved in 0.5 M PBS buffer, pH 7 at a concentration of 10 mg/mL. AF488, NHS ester dissolved in DMSO (2 mg/mL) was added in a 20-fold molar excess and incubated at room temperature for 30 minutes in the dark. Free dye was removed by SEC under standard conditions. The resulting PEG-AF488 had a DOL of 5.7.

PEG-FAM is obtained by the same procedure using NHS-fluorescein (NHS-FAM).

Step B: Coupling of CD4 Antibody with PEG-AF488

PEG-AF488 (2.5 mg/mL in phosphate buffered saline) as obtained in step A was activated by addition of 10-fold molar excess SMCC and incubation at room temperature for 1 h. In parallel CD4 antibody (clone Vit 4) was reduced by reacting with 10 mmol/L dithiothreitol for 1 h. Maleimide activated PEG-AF488 and reduced antibody were both subjected to buffer exchange with phosphate buffered saline, pH 7.2 containing 2 mM EDTA over Sephadex G25. Maleimide activated PEG-AF488 was added to reduced antibody at a 15-fold excess and incubated for 1 h at room temperature in the dark. The reaction product is purified by SEC. The resulting CD4-PEG-AF488 had a DOL of 13.2.

CD4 is coupled to PEG-FAM using the same protocol.

Step C: Staining of PBMC with CD4 Antibody Conjugated to Fluorochromes Multimerized on 8-Arm PEG For staining experiments $10^6$ peripheral blood mononuclear cells (PBMC) each are resuspended in 100 µl phosphate buffered saline containing 2 mM EDTA and 0.5% BSA. Cells are stained with the respective CD4 antibody conjugates as obtained in step B at 3 µg/mL and incubated for 10 minutes at room temperature. Counterstaining is performed with CD3-APC and propidium iodide for dead cell exclusion.

Commercially available CD4 antibody conjugated with R-phycoerythrin (PE) or non-multimerized fluorochromes FITC or AF488 is used for comparison.

Figure 1A:
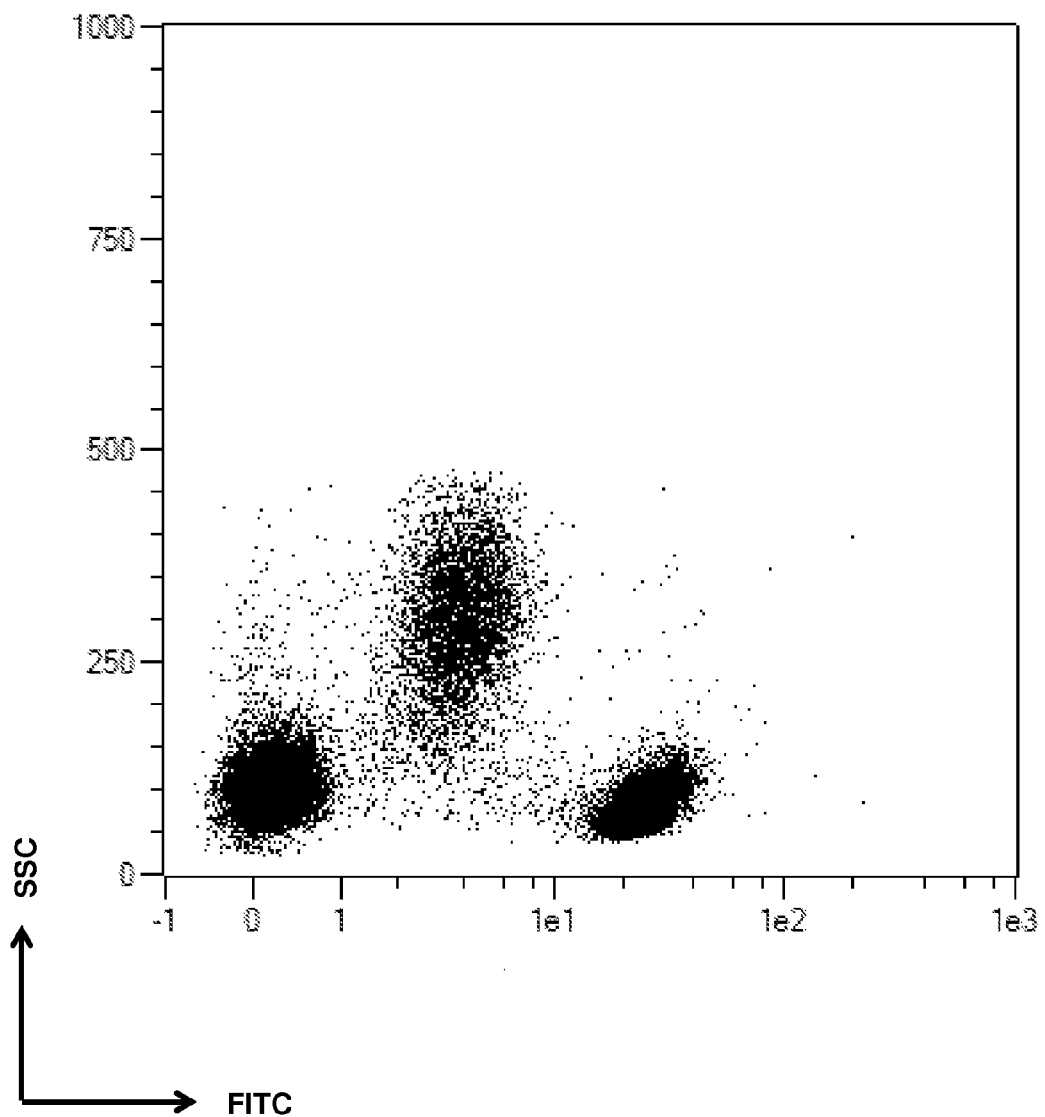
Figure 1B:
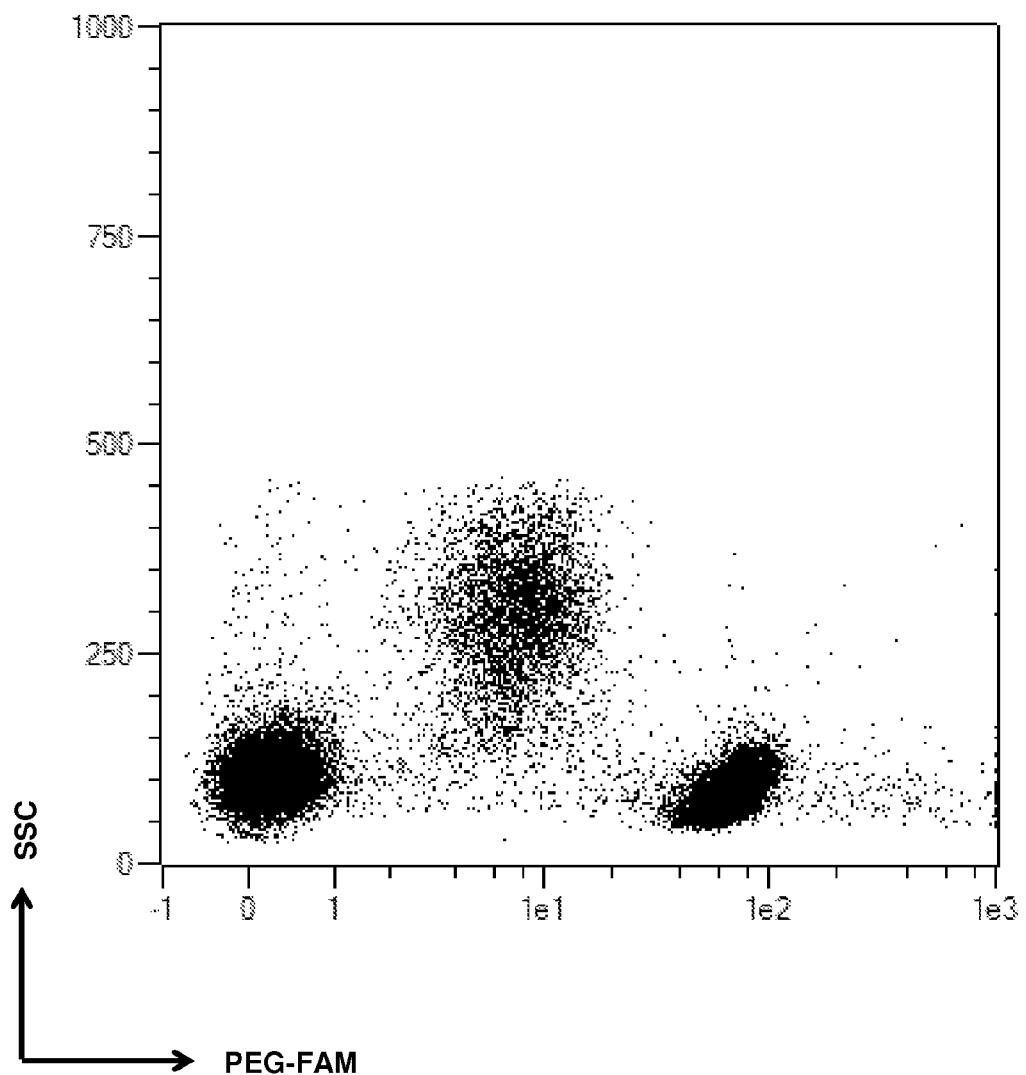
Figure 1C:
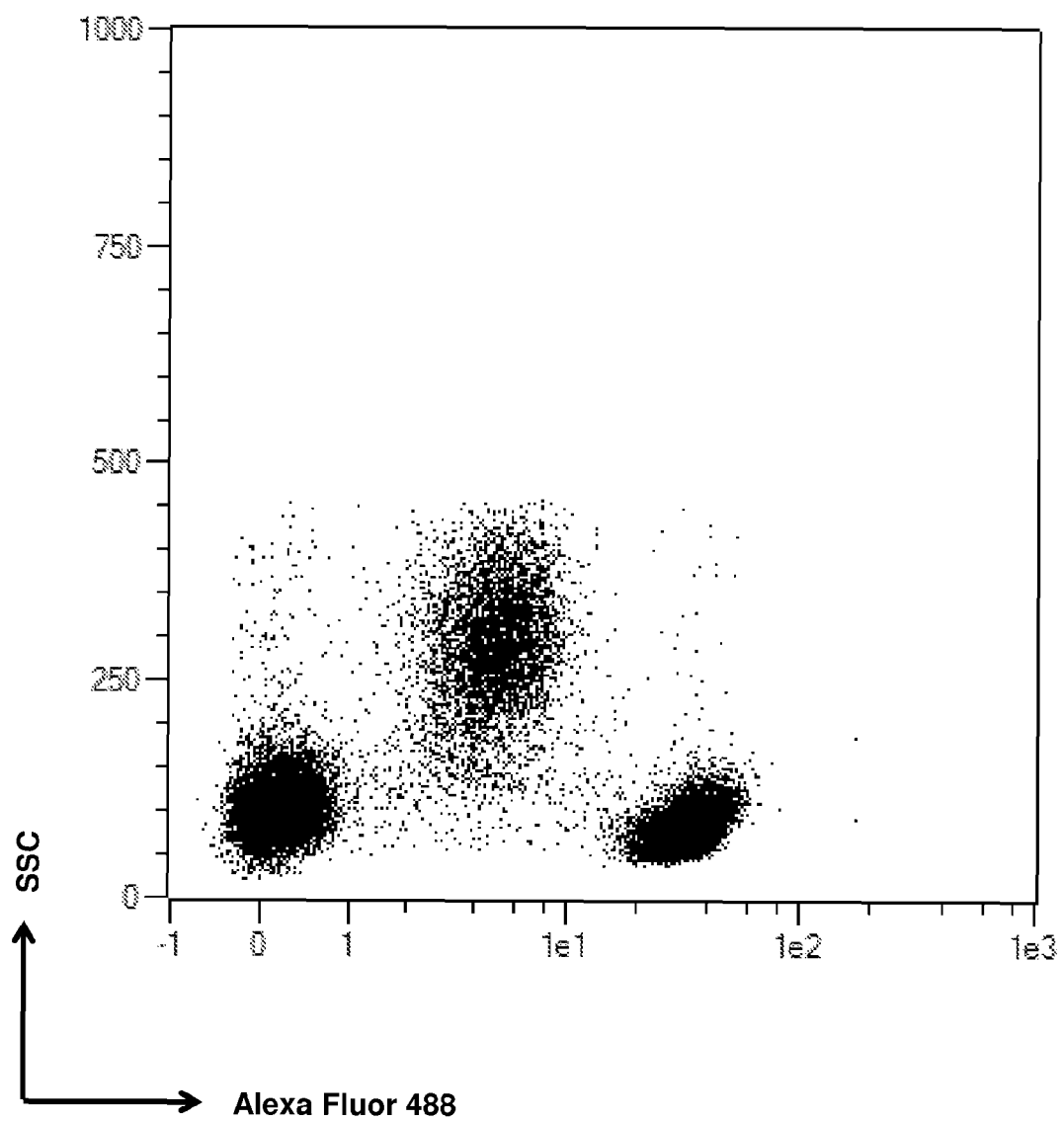
Figure 1D:
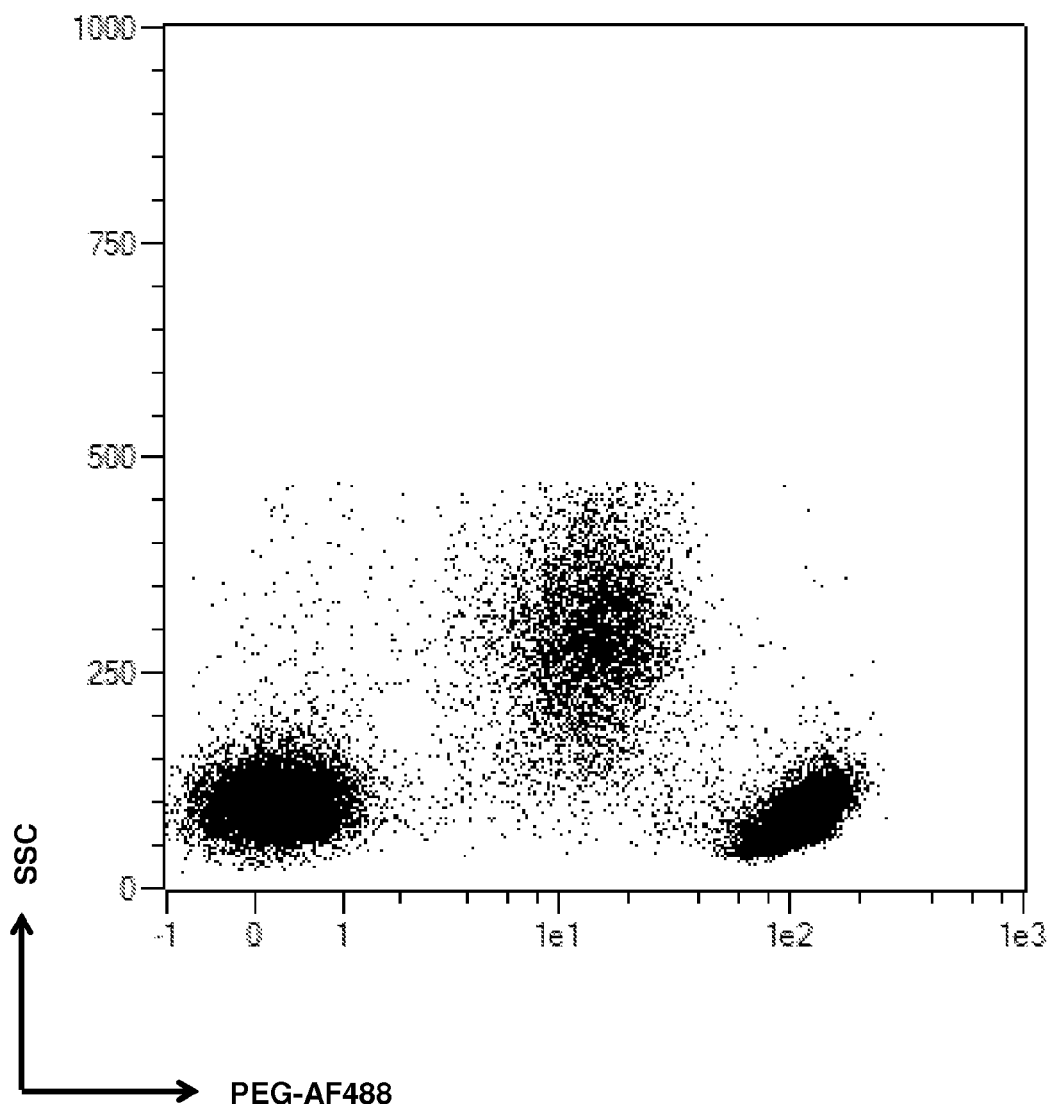
Figure 1E:
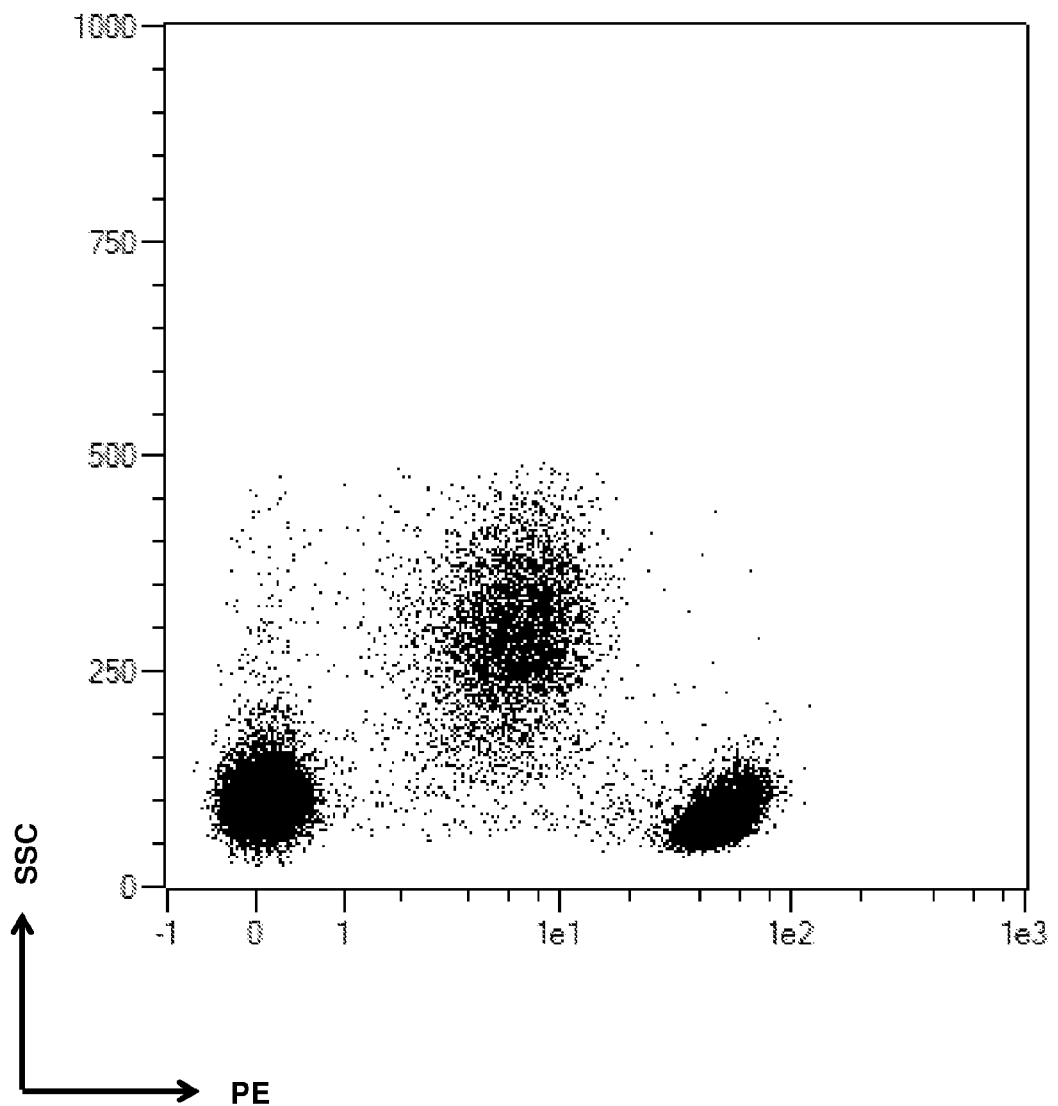

Cells are incubated 10 minutes at room temperature in the dark. Washing is performed by centrifugation and resuspension in 1 ml phosphate buffered saline containing 2 mM EDTA and 0.5% BSA. Stained cells are analyzed on the MACSQuant 10 analyzer. FIG. 1 shows dot plot examples of fluorescence intensities versus side scatter (SSC) using the following: FIG. 1a fluorescein isothiocyanate (FITC); FIG. 1b fluorescein multimerized with a branched PEG (PEG-FAM); FIG. 1c Alexa Fluor 488 (AF488); FIG. 1d Alexa Fluor 488 multimerized with a branched PEG (PEG-AF488), and FIG. 1e R-phycoerythrin (PE) and measured by flow cytometry.

FIG. 2 shows the median fluorescent intensities (MFI) and stain index (SI) results for PBMCs of 5 donors.

Figure 3:
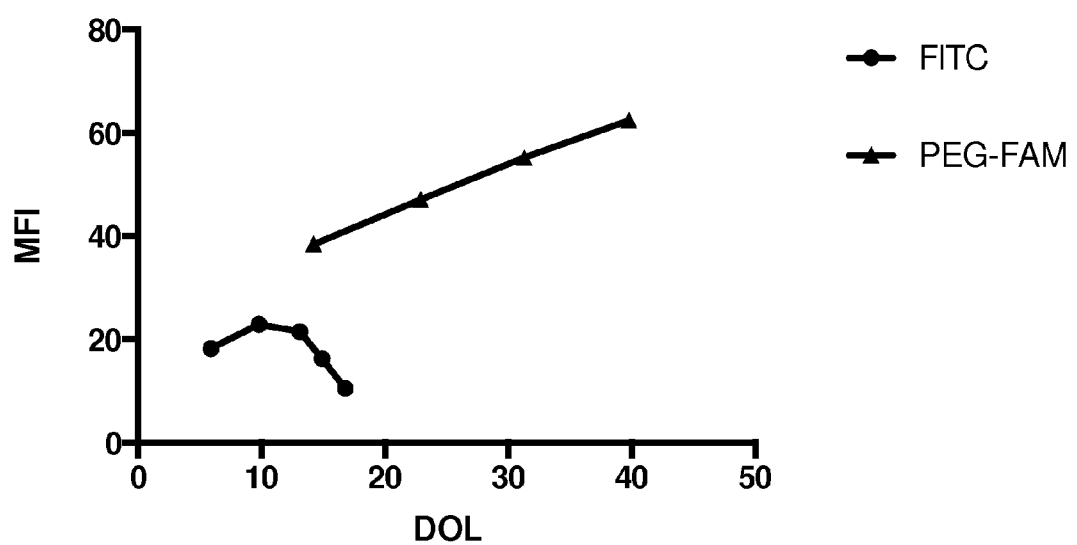
FIG. 3 shows the effect of an increasing DOL on the staining of T helper cells for fluorescein multimerized on an eight-branch polyethylene glycol (PEG-FAM) conjugated to an antibody against human CD4 (clone Vit4) in comparison to the staining with said antibody against CD4, which is conjugated to conventional fluorescein isothiocyanate (FITC). Antibody staining concentration is 3 µg/mL in all cases.

Cells stained with antibody labeled with fluorochromes according to the invention are at least twice as bright as cells stained with antibody labeled with the parent fluorochromes and on par with cells labeled with phycobiliprotein labeled antibody (CD4-PE). FIG. 3 shows the effect of an increasing DOL on the staining of T helper cells for fluorescein multimerized on an eight-branch polyethylene glycol (PEG-FAM) conjugated to an antibody against human CD4 (clone Vit4) in comparison to the staining with said antibody against CD4, which is conjugated to conventional fluorescein isothiocyanate (FITC). Antibody staining concentration is 3 μg/mL in all cases.

It is especially advantageous if the fluorochrome is also sulfonated as AF488 (Alexa Fluor). The resulting antibody conjugate labeled with AF488 multimerized on a 8-arm PEG (PEG-AF488) is about twice as bright as the corresponding conjugate made from fluorescein multimerized on a 8-arm PEG.

Example 2

Influence of Methanol Fixation on Staining Intensities

Figure 4A:
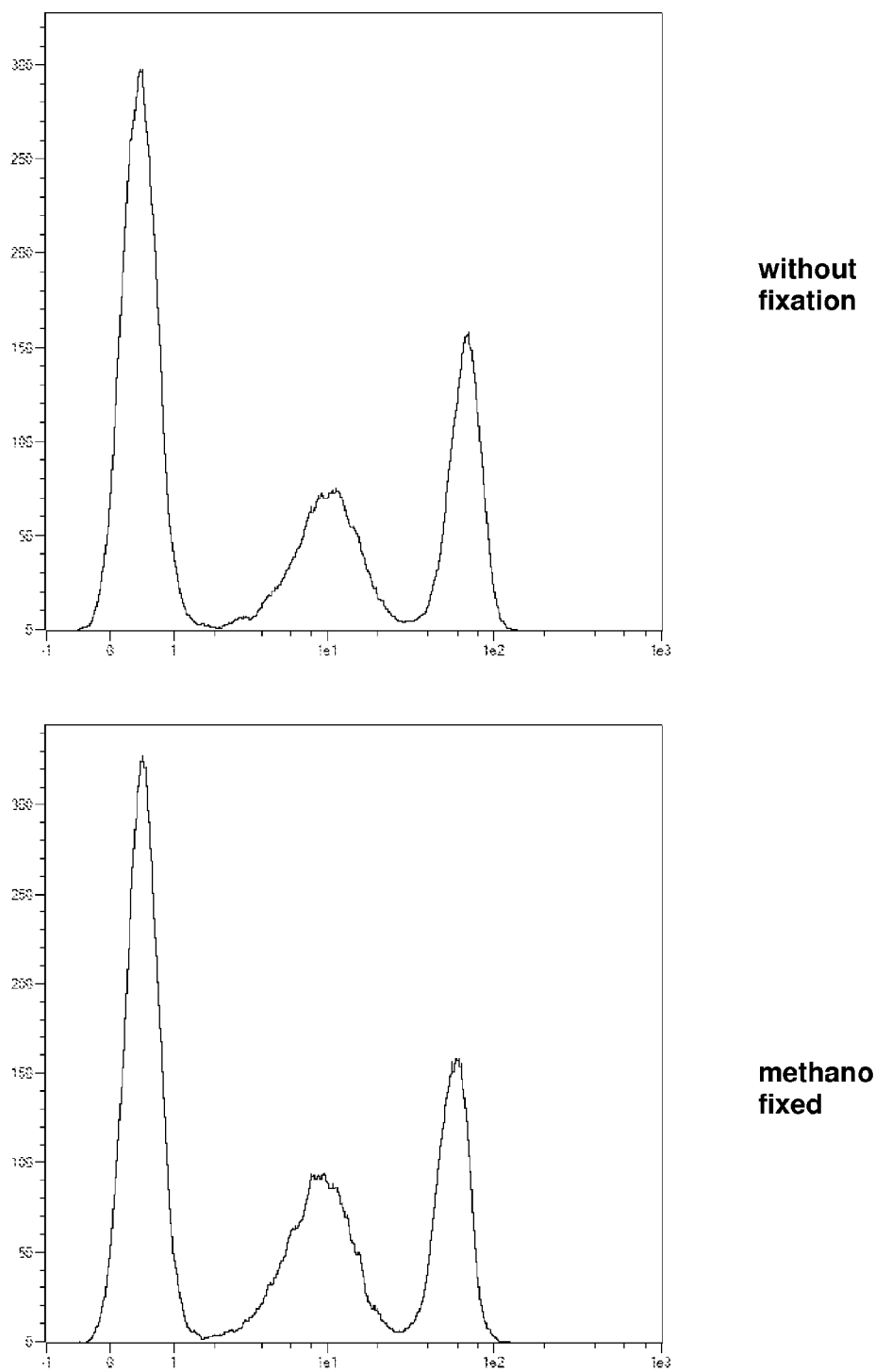
FIG. 4a shows histogram plots of CD4-PEG-FAM stained non-fixed and methanol fixed T helper cells.
Figure 4B:
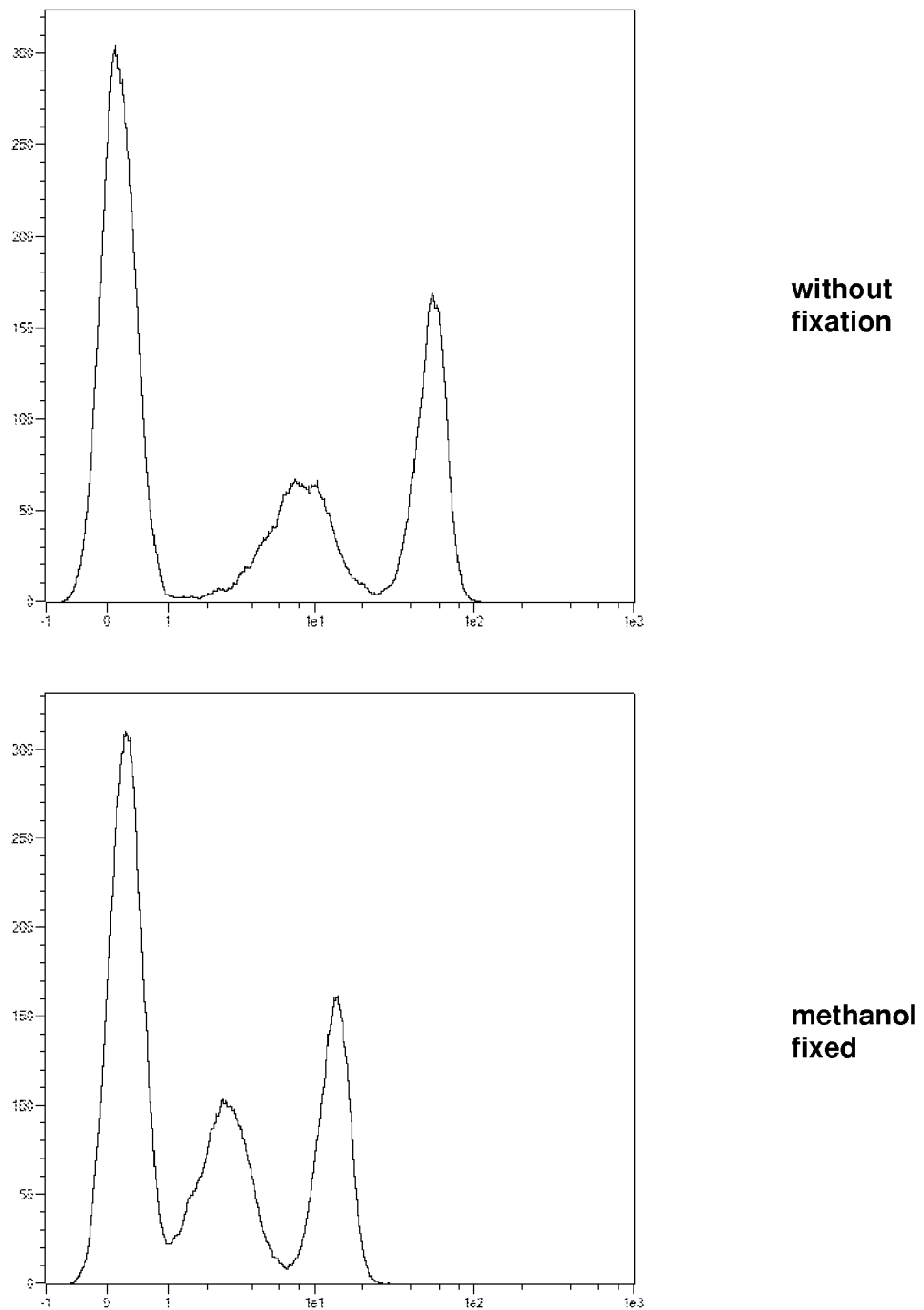
FIG. 4b shows CD4-PE stained non-fixed and methanol fixed T helper cells.

Peripheral blood mononuclear cells are stained as described in example 1 excluding propidium iodide as counterstain. For methanol fixation 1 mL methanol is added to 100 μL cell suspension and incubated for 30 minutes on ice. Cells are washed twice with and resuspended in 1 mL phosphate buffered saline containing 2 mM EDTA and 0.5% BSA. Stained and fixed cells are analyzed on the MACSQuant 10 analyzer in comparison to non-fixed cells. FIGS. 4a and 4b show histogram plots of CD4-PEG-FAM stained non-fixed and methanol fixed T helper cells (FIG. 4a) and CD4-PE stained non-fixed and methanol fixed T helper cells (FIG. 4b). The fluorescence intensity of CD4-PEG-FAM is stable versus methanol fixation whereas the fluorescence intensity of CD4-PE shows a five-fold decrease.

Accordingly, the fluorescent biomolecule conjugates and/or the fluorescent dyes of the invention show improved stability towards environmental influences such as fixation.

While various details have been described in conjunction with the exemplary implementations outlined above, various alternatives, modifications, variations, improvements, and/or substantial equivalents, whether known or that are or may be presently unforeseen, may become apparent upon reviewing the foregoing disclosure. Accordingly, the exemplary implementations set forth above, are intended to be illustrative, not limiting.

What is claimed is:
1. A fluorescent dye according to the formula III:

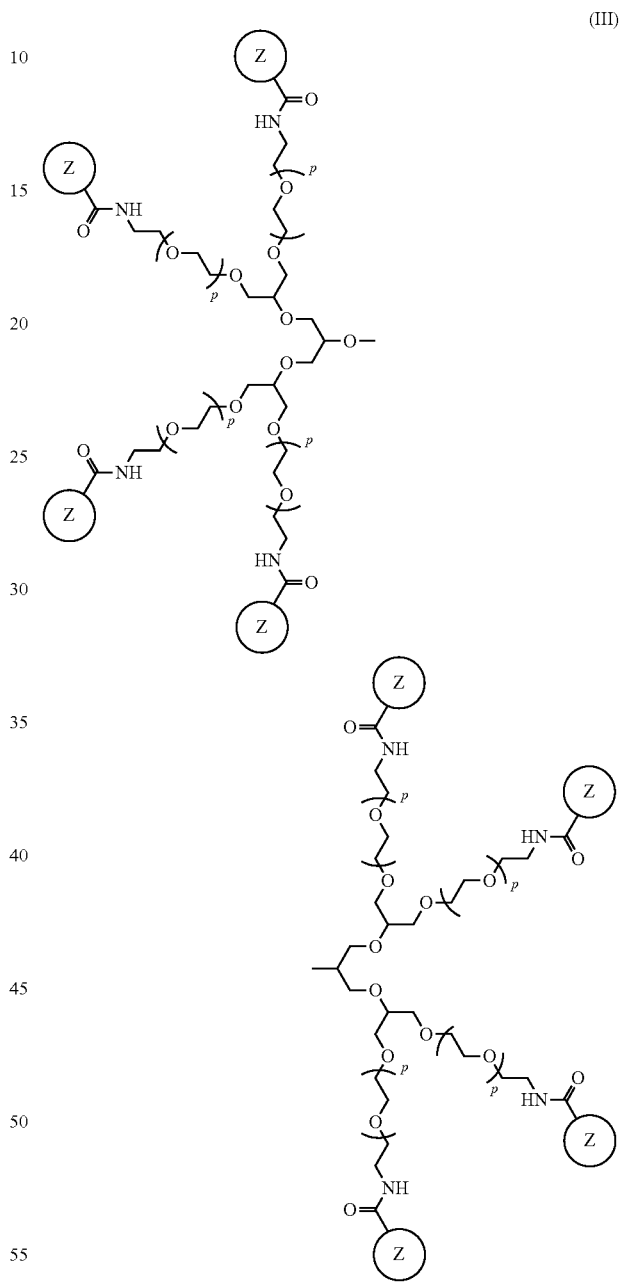

(III)

wherein
p is an integer ranging from 10 to 200;
Z is at least one of F and R, with
    F comprises same or different fluorophores covalently bound to the residues $CH_2CH_2O$—
    R comprises a reactive group selected from the group consisting of N-hydroxysuccinimid ester, tetrafluorophenyl ester, pentafluorophenyl ester, sulfodichlorophenyl ester, imido ester, isothiocyanate, isocyanate, sulfonyl halides, acyl halides, acyl azide, monochlorotriazine, dichlorotriazine, aldehyde, glyoxal, maleimide, iodoacetamide, hydrazine, azidonitrophenyl, phosphoramidite, alkyne, alkyl azide, dienes and allyl groups;

with the provision that general formula (III) comprises at least two F and at least one group R.

2. The fluorescent dye according to claim 1, wherein the fluorophore F is selected from the group consisting of xanthene dyes, rhodamine dyes, coumarine dyes, cyanine dyes, pyrene dyes, oxazine dyes, pyridyl oxazole dyes and pyrromethene dyes.

3. The fluorescent dye according to claim 1, wherein the fluorophore F is substituted with one more water solubility imparting substituents selected from the group consisting of sulfonates, phosphonates, phosphates, sulfonamides, polyethers and carbonates.

4. A fluorescent biomolecule conjugate comprising at least one fluorescent dye according claim 1, wherein a biomolecule is conjugated via group R to the at least one fluorescent dye, and the biomolecule is selected from group consisting of immunoglobulin, antibody, fragmented antibody, Fab, Fab', F(ab')$_2$, sdAb, scFv, di-scFv each of naturally or recombinant origin.

5. A fluorescent biomolecule conjugate comprising at least one fluorescent dye according claim 1, wherein a biomolecule is conjugated via group R to the at least one fluorescent dye, and the biomolecule is selected from the group consisting of peptide/MHC-complexes, receptors for cell adhesion or costimulatory molecules, receptor ligands, antigens, hapten binders, avidin, streptavidin, neutravidin, aptamers, primers and ligase substrates.

6. A fluorescent biomolecule conjugate comprising at least one fluorescent dye according claim 1, wherein a biomolecule is conjugated with 2 to 20 fluorescent dyes according to claim 1, each fluorescent dye comprising between 1 and 10 fluorophores F, inclusive.

7. A method of analyzing cells or tissue, comprising:
  labeling with the fluorescent biomolecule conjugate according to claim 4; and
  performing at least one of flow cytometry and fluorescence microscopy.

* * * * *